(12) United States Patent
Bodduluri et al.

(10) Patent No.: US 12,246,192 B2
(45) Date of Patent: Mar. 11, 2025

(54) INVERSE PLANNING DEVICE AND METHODS FOR RADIATION TREATMENT

(71) Applicant: Zap Surgical Systems, Inc., San Carlos, CA (US)

(72) Inventors: Radhika Mohan Bodduluri, Palo Alto, CA (US); Thibaut Loysel, Redwood City, CA (US); Achim Schweikard, Lubeck (DE); John R. Adler, Jr., Stanford, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 233 days.

(21) Appl. No.: 17/590,609

(22) Filed: Feb. 1, 2022

(65) Prior Publication Data

US 2022/0241613 A1 Aug. 4, 2022

Related U.S. Application Data

(60) Provisional application No. 63/213,380, filed on Jun. 22, 2021, provisional application No. 63/144,411, filed on Feb. 1, 2021.

(51) Int. Cl.
*A61N 5/10* (2006.01)

(52) U.S. Cl.
CPC .......... *A61N 5/1039* (2013.01); *A61N 5/1049* (2013.01); *A61N 2005/1074* (2013.01)

(58) Field of Classification Search
CPC ................ A61N 5/1039; A61N 5/1049; A61N 2005/1074; A61N 5/103
See application file for complete search history.

(56) References Cited

U.S. PATENT DOCUMENTS 2,595,260 A 5/1952 Hollstein
2,781,454 A 2/1957 Green et al.
(Continued)

FOREIGN PATENT DOCUMENTS

CN 2533895 Y 2/2003
CN 1481756 A 3/2004
(Continued)

OTHER PUBLICATIONS

Bodduluri et al., "X-ray guided robotic radiosurgery for solid tumors", Industrial Robot: An International Journal, vol. 29, No. 3, 2002, pp. 221-227.
(Continued)

*Primary Examiner* — Kiho Kim
(74) *Attorney, Agent, or Firm* — Kilpatrick Townsend & Stockton LLP (57) ABSTRACT

Devices and methods that allow a user to elect between performing treatment planning by inverse planning or to be accomplished by utilizing one or more parameters input that are typically associated with forward planning are described herein. The systems can be configured to produce a treatment plan in a single iteration upon initiation of treatment planning or in response to determining or receiving a target geometry. While the system may be used iteratively in an extensively interactive fashion, viable inverse plans can be generated with a single user interaction, such as a single click, or optionally with no click at all. Advantageously, the system can optionally allows a clinician to add or adjust parameters or constraints, for example in another iteration, to provide additional autonomy if desired.

28 Claims, 6 Drawing Sheets

(56) References Cited

U.S. PATENT DOCUMENTS

| | | |
|---|---|---|
| 2,818,510 A | 12/1957 | Hansheinrich |
| 2,890,349 A | 6/1959 | Laszlo |
| 3,082,322 A | 3/1963 | Koerner et al. |
| 3,281,598 A | 10/1966 | Irene |
| 3,349,242 A | 10/1967 | Braestrup |
| 3,466,439 A | 9/1969 | Setala |
| 3,488,495 A | 1/1970 | Schneeman |
| 3,588,499 A | 6/1971 | Pegrum |
| 3,617,749 A | 11/1971 | Massiot |
| 3,670,163 A | 6/1972 | Lajus |
| 3,803,418 A | 4/1974 | Holstrom |
| 3,833,813 A | 9/1974 | James |
| 3,852,598 A | 12/1974 | Larsson |
| 3,868,506 A | 2/1975 | Ogiso |
| 3,892,967 A | 7/1975 | Howarth et al. |
| 4,139,775 A | 2/1979 | Williams |
| 4,177,382 A | 12/1979 | Hounsfield |
| 4,209,706 A | 6/1980 | Nunan |
| 4,266,135 A | 5/1981 | Kuwik et al. |
| 4,288,700 A | 9/1981 | Grass et al. |
| 4,338,521 A | 7/1982 | Shaw et al. |
| 4,339,825 A | 7/1982 | Barrett et al. |
| 4,358,856 A | 11/1982 | Stivender et al. |
| 4,363,128 A | 12/1982 | Grady et al. |
| 4,481,656 A | 11/1984 | Janssen et al. |
| 4,541,108 A | 9/1985 | Grady et al. |
| 4,560,882 A | 12/1985 | Barbaric et al. |
| 4,649,560 A | 3/1987 | Grady et al. |
| 4,653,083 A | 3/1987 | Rossi |
| 4,741,015 A | 4/1988 | Charrier |
| 4,741,105 A | 5/1988 | Wong |
| 4,756,016 A | 7/1988 | Grady et al. |
| 4,827,491 A | 5/1989 | Barish |
| 4,866,751 A | 9/1989 | Louiday |
| 4,922,512 A | 5/1990 | Lajus et al. |
| 4,977,585 A | 12/1990 | Boyd |
| 4,987,585 A | 1/1991 | Kidd et al. |
| 4,998,268 A | 3/1991 | Winter |
| 5,038,371 A | 8/1991 | Janssen et al. |
| 5,040,203 A | 8/1991 | Janssen et al. |
| 5,048,069 A | 9/1991 | Siczek |
| 5,048,071 A | 9/1991 | Van |
| 5,052,036 A | 9/1991 | Grady |
| 5,054,041 A | 10/1991 | Hampel |
| 5,073,917 A | 12/1991 | Van et al. |
| 5,086,447 A | 2/1992 | Siczek et al. |
| 5,095,501 A | 3/1992 | Kobayashi |
| 5,155,757 A | 10/1992 | Sakaniwa et al. |
| 5,159,622 A | 10/1992 | Sakaniwa et al. |
| 5,207,223 A | 5/1993 | Adler et al. |
| 5,379,333 A | 1/1995 | Toth |
| 5,420,427 A | 5/1995 | Morgan et al. |
| 5,537,452 A | 7/1996 | Shepherd et al. |
| 5,577,094 A | 11/1996 | Fudamoto |
| 5,634,929 A | 6/1997 | Misko et al. |
| 5,699,446 A | 12/1997 | Rougee et al. |
| 5,751,781 A | 5/1998 | Brown et al. |
| 5,835,557 A | 11/1998 | Malmstroem |
| 5,945,684 A | 8/1999 | Lam et al. |
| 5,960,411 A | 9/1999 | Hartman et al. |
| 6,104,779 A | 8/2000 | Shepherd et al. |
| 6,155,713 A | 12/2000 | Watanabe |
| 6,198,957 B1 | 3/2001 | Green |
| 6,217,214 B1 | 4/2001 | Cabral et al. |
| 6,309,102 B1 | 10/2001 | Stenfors |
| 6,325,538 B1 | 12/2001 | Heesch |
| 6,614,871 B1 | 9/2003 | Kobiki et al. |
| 6,789,941 B1 | 9/2004 | Grady |
| 6,856,670 B2 | 2/2005 | Hoheisel |
| 6,888,919 B2 | 5/2005 | Graf |
| 6,969,194 B1 | 11/2005 | Naefstadius |
| 7,188,999 B2 | 3/2007 | Mihara et al. |
| 7,193,227 B2 | 3/2007 | Hiramoto et al. |
| 7,239,684 B2 | 7/2007 | Hara et al. |
| 7,295,648 B2 | 11/2007 | Brown |
| 7,298,819 B2 | 11/2007 | Dooley et al. |
| 7,302,038 B2 | 11/2007 | Mackie et al. |
| 7,473,913 B2 | 1/2009 | Hermann et al. |
| 7,502,443 B1 | 3/2009 | Haynes et al. |
| 7,526,066 B2 | 4/2009 | Koshnitsky et al. |
| 7,649,981 B2 | 1/2010 | Seppi et al. |
| 8,139,714 B1 | 3/2012 | Sahadevan |
| 8,337,382 B2 | 12/2012 | Schneider et al. |
| 8,406,844 B2 | 3/2013 | Ruchala et al. |
| 8,602,647 B2 | 12/2013 | Navarro |
| 8,747,292 B2 | 6/2014 | Schneider et al. |
| 8,913,716 B2 | 12/2014 | Sobering et al. |
| 9,014,341 B2 | 4/2015 | Zhang et al. |
| 9,208,918 B2 | 12/2015 | Tybinkowski et al. |
| 9,308,395 B2 | 4/2016 | Adler, Jr. et al. |
| 9,314,160 B2 | 4/2016 | Adler, Jr. et al. |
| 9,604,077 B2 | 3/2017 | Xing et al. |
| 9,757,593 B2 | 9/2017 | Adler et al. |
| 9,808,651 B2 | 11/2017 | Schneider et al. |
| 10,499,861 B2 | 12/2019 | Achkire et al. |
| 11,058,892 B2 | 7/2021 | Wilbur et al. |
| 2004/0066889 A1 | 4/2004 | Swift |
| 2004/0149924 A1 | 8/2004 | Russell |
| 2004/0170254 A1 | 9/2004 | Gregerson et al. |
| 2004/0251419 A1 | 12/2004 | Nelson et al. |
| 2005/0049477 A1 | 3/2005 | Fu et al. |
| 2005/0197564 A1 | 9/2005 | Dempsey |
| 2005/0236588 A1 | 10/2005 | Ein-Gal |
| 2006/0245548 A1 | 11/2006 | Callerame et al. |
| 2007/0014391 A1 | 1/2007 | Mostafavi et al. |
| 2007/0041500 A1 | 2/2007 | Olivera et al. |
| 2007/0189591 A1 | 8/2007 | Lu et al. |
| 2008/0002809 A1 | 1/2008 | Bodduluri |
| 2008/0144908 A1 | 6/2008 | West et al. |
| 2008/0212738 A1 | 9/2008 | Gertner et al. |
| 2009/0080602 A1* | 3/2009 | Brooks .............. A61B 6/4258 378/65 |
| 2009/0086909 A1 | 4/2009 | Hui et al. |
| 2009/0103686 A1 | 4/2009 | Rothschild |
| 2009/0110146 A1 | 4/2009 | Sliski et al. |
| 2009/0163799 A1 | 6/2009 | Erbel et al. |
| 2009/0180678 A1 | 7/2009 | Kuduvalli et al. |
| 2010/0002829 A1 | 1/2010 | Dafni |
| 2010/0094119 A1 | 4/2010 | Yu et al. |
| 2010/0183196 A1 | 7/2010 | Fu et al. |
| 2010/0237259 A1 | 9/2010 | Wang |
| 2010/0239066 A1 | 9/2010 | Conolly et al. |
| 2010/0268074 A1 | 10/2010 | Van Loef et al. |
| 2011/0210261 A1 | 9/2011 | Maurer, Jr. |
| 2012/0053961 A1 | 3/2012 | Wang et al. |
| 2013/0114872 A1 | 5/2013 | Chen et al. |
| 2013/0136239 A1 | 5/2013 | Laws et al. |
| 2013/0188856 A1 | 7/2013 | Adler, Jr. et al. |
| 2013/0261430 A1 | 10/2013 | Uhlemann |
| 2014/0140471 A1 | 5/2014 | Tybinkowski et al. |
| 2014/0350322 A1 | 11/2014 | Schulte et al. |
| 2015/0141733 A1 | 5/2015 | Kumar et al. |
| 2016/0095558 A1 | 4/2016 | Choy et al. |
| 2016/0144201 A1* | 5/2016 | Schulte .............. A61N 5/1084 600/1 |
| 2016/0220848 A1 | 8/2016 | Adler, Jr. et al. |
| 2016/0317839 A1 | 11/2016 | Prionas et al. |
| 2017/0281972 A1 | 10/2017 | Zhang et al. |
| 2018/0318607 A1 | 11/2018 | Wilbur et al. |
| 2018/0369611 A1 | 12/2018 | Owens et al. |
| 2019/0001146 A1 | 1/2019 | Liu |
| 2019/0069856 A1 | 3/2019 | Achkire et al. |
| 2019/0366123 A1 | 12/2019 | Adler, Jr. et al. |
| 2020/0038685 A1 | 2/2020 | Kundapur et al. |
| 2020/0121954 A1 | 4/2020 | Bodduluri et al. |
| 2020/0241613 A1 | 7/2020 | Lakshman et al. |
| 2020/0294678 A1 | 9/2020 | Camuso-Gianella et al. |
| 2020/0398083 A1 | 12/2020 | Adelsheim |

FOREIGN PATENT DOCUMENTS

| | | |
|---|---|---|
| CN | 1666301 A | 9/2005 |
| CN | 2772541 Y | 4/2006 |
| CN | 1785454 A | 6/2006 |

(56) References Cited

FOREIGN PATENT DOCUMENTS

| | | |
|---|---|---|
| CN | 1919372 A | 2/2007 |
| CN | 101069644 A | 11/2007 |
| CN | 101496727 A | 8/2009 |
| CN | 102441238 A | 5/2012 |
| CN | 103185914 A | 7/2013 |
| CN | 106237545 A | 12/2016 |
| CN | 106267587 A | 1/2017 |
| CN | 106456991 A | 2/2017 |
| CN | 106512221 A | 3/2017 |
| CN | 106908827 A | 6/2017 |
| CN | 107101712 A | 8/2017 |
| CN | 107297032 A | 10/2017 |
| CN | 108401421 A | 8/2018 |
| CN | 304866064 S | 10/2018 |
| DE | 3321057 A1 | 12/1984 |
| DE | 19728788 A1 | 1/1999 |
| EM | 0047419320001 | 3/2018 |
| EP | 1075855 A1 | 2/2001 |
| FR | 1587608 A | 3/1970 |
| GB | 1129653 A | 10/1968 |
| JP | 6082300 U | 6/1985 |
| JP | 01502401 A | 8/1989 |
| JP | 04221532 A | 8/1992 |
| JP | 2885304 B2 | 12/1993 |
| JP | 0767975 A | 3/1995 |
| JP | 07163669 A | 6/1995 |
| JP | H07255867 A | 10/1995 |
| JP | H07265445 A | 10/1995 |
| JP | 2000271109 A | 10/2000 |
| JP | 2001137372 A | 5/2001 |
| JP | 2003024459 A | 1/2003 |
| JP | 2003205042 A | 7/2003 |
| JP | 2003210596 A | 7/2003 |
| JP | 2004097646 A | 4/2004 |
| JP | 2007148276 A | 6/2007 |
| JP | 2010519965 A | 6/2010 |
| JP | 2012183283 A | 9/2012 |
| NL | 7215879 | 5/1973 |
| WO | 0074779 A1 | 12/2000 |
| WO | 0112262 A1 | 2/2001 |
| WO | 03018131 A1 | 3/2003 |
| WO | 2003077763 | 9/2003 |
| WO | 2008024463 A2 | 2/2008 |
| WO | 2012040964 A1 | 4/2012 |
| WO | 2013180883 A1 | 12/2013 |
| WO | 2015096572 A1 | 7/2015 |
| WO | 2017020244 A1 | 2/2017 |
| WO | 2017041750 A1 | 3/2017 |
| WO | 2017083026 A1 | 5/2017 |
| WO | 2017100611 A1 | 6/2017 |
| WO | 2018/203918 A1 | 11/2018 |

OTHER PUBLICATIONS

Dong et al., "An Image Correlation Procedure for Digitally Reconstructed Radiographs and Electronic Portal Images", Int. J. Radiation Oncology Biol. Phys., vol. 33, No. 5, 1995, pp. 1053-1060.
Hissoiny et al., "GPUMCD: a new GPU-Oriented Monte Carlo dose calculation platform", physics.med-ph, Jan. 2011, 28 pp.
Jung et al., "Flexible Gd2O2S:Tb scintillators pixelated with polyethylene microstructures for digital x-ray image sensors", J. Micromech. Microeng. 19, 2009, 10pp.
Lo et al., "Hardware acceleration of a Monte Carlo simulation for photodynamic treatment planning", Journal of Biomedical Optics, vol. 14(1), Jan./Feb. 2009, pp. 014019-1 thru 014019-11.
Mackie et al., "Tomotherapy: a new concept for the delivery of dynamic conformal radiotherapy.", Medical Physics 20, 1709 (1993); doi: 10.1118/1.596958, Jun. 4, 1998, 1709-1719.
Osher et al., "Fast Linearized Bregman Iteration for Compressive Sensing and Sparse Denoising", 2008, pp. 1-19.
Ruchala et al., "Megavoltage CT image reconstruction during tomotherapy treatments", Phys. Med. Biol. vol. 45, 2000, pp. 3545-3562.
Schonberg , "The History of the Portable Linear Accelerator", American Association for Physicists in Medicine, downloaded from the internet: https://www.aapm.org/meetings/2001AM/pdf/7221-68900.pdf, 2001, pp. 1-14.
Weidlich et al., "Characterization of a Novel Revolving Radiation Collimator", Cureus, vol. 10, No. 2, Feb. 2, 2018, pp. 1-9.
Zaman et al., "Scintillating Balloon-Enabled Fiber-Optic System for Radionuclide Imaging of Atherosclerotic Plaques", J Nucl Med 56(5), 2015, 771-777.

\* cited by examiner

Multiple Beams B
300

Tumor T 320
Critical Structures C
310

INVERSE PLANNING DEVICE AND METHODS FOR RADIATION TREATMENT

CROSS-REFERENCES TO RELATED APPLICATIONS

The present application claims the benefit under 35 USC § 119(e) of U.S. Provisional Appln Nos. 63/144,411 filed Feb. 1, 2021 and 63/213,380 filed Jun. 22, 2021; the full disclosures which are incorporated herein by reference in their entirety for all purposes.

FIELD OF THE INVENTION

The present invention is generally related to the fields of radiation therapy and stereotactic radiosurgery, and can also be applied to the delivery of ultrasound, and other energy-based treatments.

BACKGROUND

Stereotactic radiosurgery and some forms of radiation therapy involve beams of ionizing radiation generated outside of a patient which is precisely aimed so as to cross paths with other radiation beams within the targeted area, for example a tumor. The goal is to produce a high dosage of radiation to the target ("prescribed dose"), a very low dose outside of the target zone, and an absolute minimum amount of radiation to certain easily injured non-targeted areas ("critical structures"). Prior to the actual delivery such a radiation treatment (which is irreversible), the number, trajectory and strength of the radiation beams must be accurately planned. Such planning is optimally accomplished by a type of computer program generally known as "treatment planning software." Treatment planning software is utilized to determine optimal radiation beam positions, beam orientations, beam shapes, beam intensities, and radiation dose distributions within the patient needed to deliver sufficient radiation to the target, and acceptable amounts of stray radiation to non-target regions. Utilizing the treatment planning software to inform decisions of treatment planning, the user subsequently selects/decides upon the ultimate treatment plan to be delivered by the system.

Broadly, there are two approaches to radiation treatment planning: forward planning and inverse planning. In forward treatment planning, a user (such as a medical physicist, technician or radiosurgeon-physician) determines the radiation dose of a chosen beam and then calculates how much radiation will be absorbed by the tumor, critical structures (i.e., vital organs) and other healthy tissue. The user estimate, based upon experience, required values for various treatment parameters, such as beam positions and beam intensities. The treatment planning system then calculates the resulting dose distribution. After reviewing the resulting dose distribution, these may be iteratively modified until a solution acceptable to the user is reached.

Inverse planning has the advantage of being able to produce higher quality plans than forward planning, when in the hands of less experienced users. With contemporary inverse planning systems, the user independently specifies: the minimum dose to the tumor and the maximum dose to other healthy tissues. The software then selects the direction, distance, and total number, time on and intensity of the beams in order to achieve the specified dose conditions. While some have suggested treatment planning that can utilize aspects of both forward treatment planning and inverse planning approaches, these different approaches have largely each been retained as distinct and separately applied processes such that the resulting treatment planning process becomes even more complex, cumbersome and iterative than utilizing either alone. For example, U.S. Pat. No. 7,298,819, describes a system that permits a user to switch between forward planning and inverse planning techniques, to utilize forward planning for some treatment beams and inverse planning for other treatment beams, or to apply one technique to a treatment plan previously generated using the other technique. Accordingly, these treatment planning approaches thus far have failed to employ aspects of both forward planning and inverse planning in a truly integrated manner that is robust, consistent and easy to use for a variety of clinicians, including both clinicians having limited expertise and those having extensive experience.

Accordingly, current radiation treatment planning sessions are still cumbersome, time-consuming and complex, and can result in widely varying and sub-optimal treatment plans, particularly for those having limited experience. Therefore, there is a need for improved treatment planning system and methods that provide consistent, optimized treatment plans without requiring extensive input by the clinician. There is further need for such systems and methods that accommodate a wide range of clinician experience.

BRIEF SUMMARY OF THE INVENTION

The invention relates to devices and methods that allow inverse planning to be accomplished with only the target provided by the user, with the target and a prescribed dose, or with the target and optionally one or more additional parameters, constraints, or variables that are input by the user. While the system may be used iteratively in an extensively interactive fashion, viable inverse plans can be generated with the push of a single user interaction (e.g., "single click of a button"), or optionally with no click at all. In one aspect, the system provides for treatment plan generation without any clinician input constraints. In another aspect, the system provides treatment plan generation that allows for one or more clinician input constraints, including minimal input or extensive input per the clinician's preference and skill level. Accordingly, the system provides improved versatility allowing both treatment plan generation without any clinician input constraints, preferable for clinician's with limited experience, and treatment plan generation with one or more clinician input constrains, preferable for more experienced clinicians. Advantageously, the system can optionally allow additional clinician inputs, after treatment plan generation, to allow the clinician to add or adjust parameters or constraints as desired, to generate the treatment plan. Thus, the devices and methods herein provide for consistent, optimized treatment plans regardless of the skill level and experience of the clinician.

In some embodiments, the user may provide the target information and a prescription dose to the target from which the inverse plan can be determined. In another embodiment, the user may provide only the target information itself to the treatment planning software and a treatment plan is determined through inverse planning, which can then be scaled to achieve a desired treatment dose for treatment delivery. In yet another embodiment, the user can provide a target and one or more additional parameters (e.g., number of beams, beam positions, beam weights or intensities, collimator sizes, etc.), aspects often associated with forward planning techniques, then determine a treatment plan. In some embodiments, any of the above described approaches can be performed in a single iteration or process. Upon review of the resulting treatment plan, the user can adjust/modify one or more constraints, variables or parameters and perform another iteration from which an updated treatment plan is produced. In some embodiments, the treatment planning software is configured to perform treatment planning by any of the above embodiments according to the preference of the user, thereby accommodating skilled clinicians desiring more forward planning aspects and clinicians with less experience desiring more inverse planning aspects or entirely inverse planning. Accordingly, the same treatment planning software can proceed with inverse planning with only the patient imaging information and target information (and optionally the target dose) to perform inverse planning of the treatment plan, or can proceed with receiving user inputs of one or more parameters before generating the treatment plan. In this manner, the treatment planning software is versatile so as to enable treatment planning entirely by the inverse planning approach, a modified inverse planning approach with one or more parameters/variables controlled/input by the user, or an treatment planning substantially by a forward planning approach. In some embodiments, each of the treatment planning approaches can be performed, once required input(s) is received, in single iteration or process, preferably upon a single actuation or click to initiated the treatment planning process or alternatively upon receiving the target geometry (e.g., contours, segmentation) from the user, upon determining target geometry, or upon receiving adjustment or updates to target geometry. Upon generation of the treatment plan, the user can review the treatment plan and determine whether to accept or reject the treatment plan. If the treatment plan is not accepted, the user is then provided the option to request another treatment plan by the same method, or to selectively modify one or more parameters, constraints, or points of the treatment plan, which is then fed back into the automated planning and a new updated treatment plan is generated for further review by the user. Once the treatment plan is acceptable to the user, the treatment plan is then utilized in treatment delivery.

In one aspect, the invention pertains to a method for generating a treatment plan for a radiation treatment delivery planning system. The method can include receiving or obtaining, with the system, a set of patient imaging information regarding a patient; receiving or determining a target geometry based on the set of patient imaging information; receiving one or more user interactions on a user interface of the system; and automatically generating, with the system, a treatment plan based on the set of imaging information and a prescribed treatment dose in response to the one or more user interactions. In some embodiments, receiving or obtaining the set of imaging information includes loading a patient medical image of the patient record system. The target geometry is derived from the set of imaging information and can be supplied by the user or can be determined by the user with assistance from the automated system. In some embodiments, the one or more interactions include a single user interaction (e.g., pressing a "start planning" button) to initiate treatment planning. In such embodiments, automatically determining the treatment plan can include determining optimal beam geometries, beam size, and beam weight. In some embodiments, the one or more user interactions include a user interaction to initiate treatment planning and one or more additional user interactions to select or adjust one or more parameters or constraints of treatment planning. The one or more parameters can include any of: beam geometries, beam size, beam weight, or any combination thereof. Once the treatment plan is approved or confirmed by the user, the system can store the optimized system in a record and send to the treatment delivery system. In some embodiments, no user interaction is required to initiate treatment planning, for example, treatment planning can commence upon determination or receiving of target geometry (e.g., contours, segmentation).

In another aspect, the invention pertains to a system for generating a treatment plan for therapeutic radiation delivery. The system can include one or more processing modules having a memory with programming instructions recorded thereon for performing the various functions and processes described herein. The system further includes a user interface for receiving user interactions (e.g., selection/inputs) and a display for displaying user interface features (e.g., virtual buttons) or various parameters of the treatment plan. In some embodiments, the system includes a component that receives a set of patient imaging information; a user interface configured to receive one or more user interactions of one or more selections and/or inputs regarding treatment; and a planning component that automatically generates a treatment plan based on the patient imaging information and a prescribed treatment dose in response to one or more user interactions of the user interface. In some embodiments, the system is configured to generate an optimized treatment plan in response to a single user interaction (e.g., "single click"). In such embodiments, automatically determining the treatment plan can include determining optimal beam geometries, beam size, and beam weight. In some embodiments, the system is further configured to provide optional user inputs regarding one or more parameters of treatment and incorporate these inputs into automatically generating the treatment plan.

In another aspect, the system includes a planning component that is configured to automatically generate a treatment plan based on each of a plurality of factors that: maximizes the dose at the target to the prescribed dose, minimizes dose to the critical structures, and minimizes time required to deliver the treatment plan wherein the user does not need to request the segmentation or treatment planning. In some embodiments, the factors are weighted and/or prioritized, which can be pre-determined or adjusted by the user. In some embodiments, the component is further configured to automatically segment the image set into one or more of target and critical structure regions. The component can further be configured to a prescribed radiation dose for the target region.

In yet another aspect, the invention pertains to a method for generating a medical treatment plan with an automated planning generation system that includes steps of: receiving patient information regarding a patient with the system, the patient information including a patient identifier; and persistently storing the patient identifier in the system in which the treatment plan is created. The method can further include displaying information identifying the patient and/or treatment and displaying an indication of a single action that is to be performed to generate the treatment plan; and in response to the single action being performed, sending to the system a request to initiate treatment planning generation based on the patient information; and displaying the generated treatment plan to the user for confirmation by the user. Upon receiving confirmation of the plan, the treatment plan is sent to the treatment delivery system. Upon receiving input to adjust constraints or parameters by the user, the automated system repeated plan generation and displays an updated treatment plan to the user until confirmed.

DETAILED DESCRIPTION OF THE INVENTION

The invention pertains to improved methods and systems for treatment planning for radiation systems. In one aspect, the methods and systems enable a simplified approach that utilizes inverse planning and can optionally include aspects of forward planning to arrive at an optimized treatment plan with only minimal input and action required on the part of the clinician. Advantageously, the methods and systems provide options to add or change constraints or treatment parameters for those clinicians desiring more autonomy in treatment planning.

Aspects of treatment planning methods described herein can be further understood by referring to following descriptions and examples. In accordance with embodiments of the invention, inverse planning typically has three distinct steps, of which the first two are heuristic, and the third is mathematical.

Step 1 is to select a collimator that is compatible with a contoured (segmented) target. This may be accomplished by the automated system herein described, for example by analyzing the outline of the target in three dimensions and identifying the three major axes of that three-dimensional contour and multiplying that by a factor. When the factor is 1, a collimator of approximately the same size of one of the major axes of the target is selected. Additional collimators may be selected, for example, two additional collimators, typically of the next two smaller size collimators available are selected.

In Step 2, for each point in the target, the automated system creates randomly placed candidate isocenter positions. This may be accomplished by a variety of approaches, including but not limited to, selection of every point on the boundary of the target, every point within the target, the geometric "center of mass" of the target or some portion of the points in those groups. Beam trajectories are rays or lines in three-dimensional space, which reach the defined target and pass through it. The origin of these rays or lines is generally a point along the central axis of the collimator and the end of the ray may be any point following exit of the patient's anatomy. This line or ray may be defined with the three-dimensional points (x, y, z) at each of the start and the end of the beam, or at any points along the path, or by other mathematical approaches that are known in the art, including but not limited to, the slope of the line in three dimensions, defined by cartesian or by polar coordinates. For example, for beam x traveling through candidate isocenter point p, the dose $D_P = a1x1 + a2x2 + a3x3 + a4x4 + a5x5 = \Sigma x$, a, x.

In Step 3, a specific dose is assigned to the target region, then optimization takes place. Optimization determines the selection of beams to be used from the pool of candidate beams, and determines the time spent at each beam needed to deliver the desired dose from that trajectory. In some embodiments, in the context of an intensity modulation radiotherapy system, the optimization determines the intensity of beam to be turned on, in addition to duration of beam and selection of the beam for the plan.

As viewed from a mathematical standpoint, the optimization program of the inverse planning system seeks to minimize the function J(x), where J is a function of the sum of the dose contributed by each beam to the treatment plan (x). This minimizes the dose delivered by each of the many beams in the plan that collectively deliver the prescription dose Rx to the target. In one example, $\Sigma x, x_i = $ Total dose ($x_1, x_2, x_3 \ldots$). Constraints (C) limit which beams are selected for use, thereby determining the dose (D) achieved: $C_i(x) \geq / \leq D_i$ At the target, $C_i(x)_T \geq Rx_i$ (the prescription dose)

$C_i(x)_T \leq Rx_2$ $C_i(x)_{C1} \leq Dc_i$

Setting the constraint at a designated maximum value (for example $X_i \leq 200$ (MU)) places a limit on dose delivery by any one beam, thereby permitting stereotactic radiosurgeries characteristic low dose to areas peripheral to the target. Setting the constraint $X_i \geq 0$ includes only candidate beams with a finite, positive dose in the treatment plan, since there is no negative radiation dose.

In another aspect, each point in the target can be treated as a candidate beam isocenter, the system creating a pre-designated number of beams (e.g., 100 beams), and calculating a candidate plan in which that point is the isocenter.

In some embodiments, the system can perform any of: selecting collimator sizes to be used, selecting geometry of each beam, and selecting the MUs for each beam. It is appreciated that the automated system can perform any of the above noted functions, or any combination thereof. In some embodiments, any of the above can optionally be selected by the user, while remaining functions can be performed by the automated system. In some embodiments, in regard to selecting collimator sizes, the automated system can analyze the target and select an ideal size collimator, and additional smaller collimator sizes (e.g., two smaller sizes) can be added. Optionally, the selection of the collimator size can be changed by the user. In regard to beam geometry, the system mathematically specifies origin, target destination for each candidate beam and hence the orientation of that line in three dimensions relative to the target volume. The system can generate candidate isocenters at the target's boundary or interior. In some embodiments, this may be done randomly to achieve a near-uniform distribution statistically. Alternatively, the target volume may be divided into spatial sectors, to which candidate isocenters may be assigned. In some embodiments, the number of candidate beams is set at a relatively high-number (e.g., approximately 1000) but can optionally be changed by the user if desired. In regard to selection of MUs for each beam, constraints are set-up automatically so that the target boundary gets the prescription dose and all other locations are assigned ideal value of 0. In some embodiments, the system can utilize a linear programming technique to quickly identify the MUs for each beam. Optionally, the user can change any or all the constraints noted above.

Figure 1A:
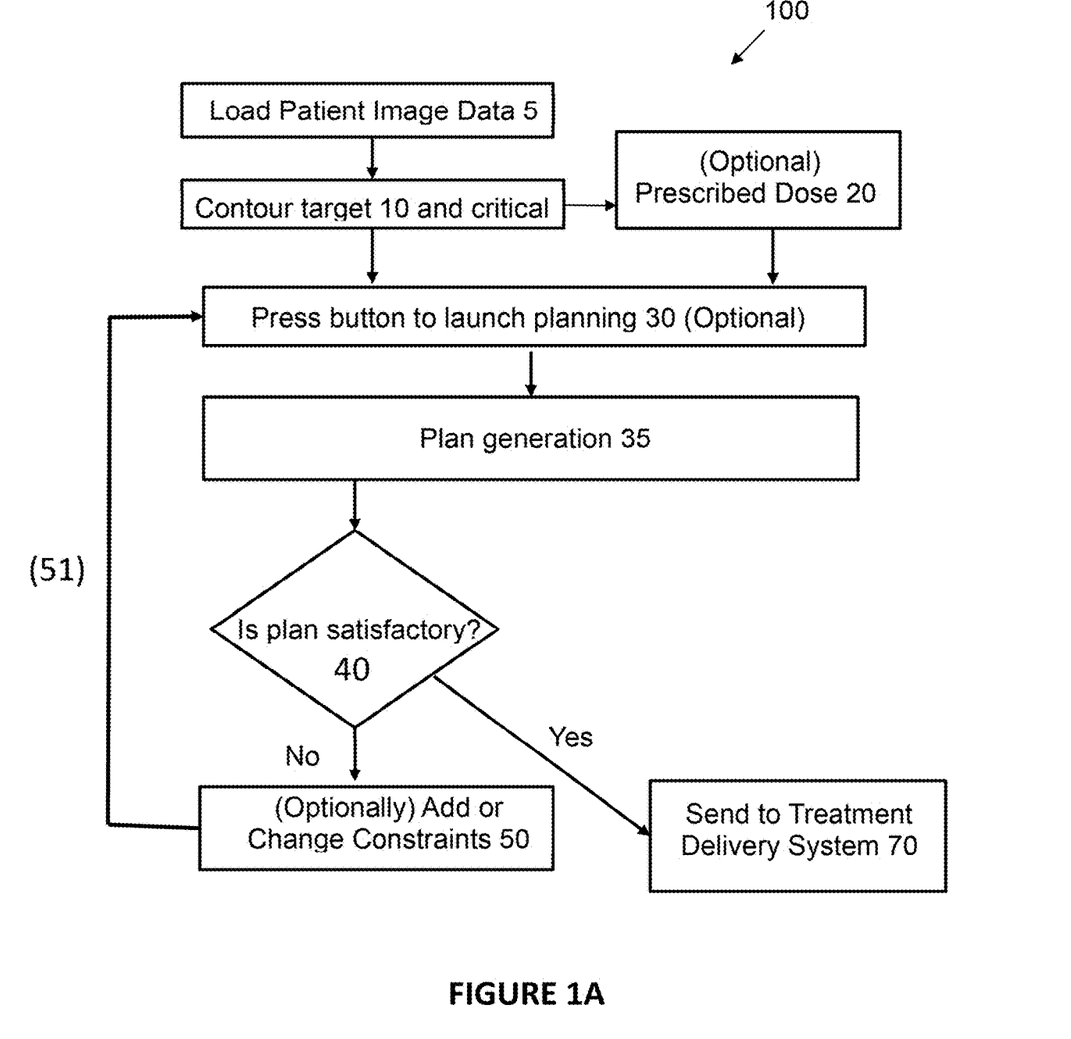
FIGS. 1A-1B illustrate exemplary methods of treatment planning, in accordance with some embodiments.
Figure 1B:
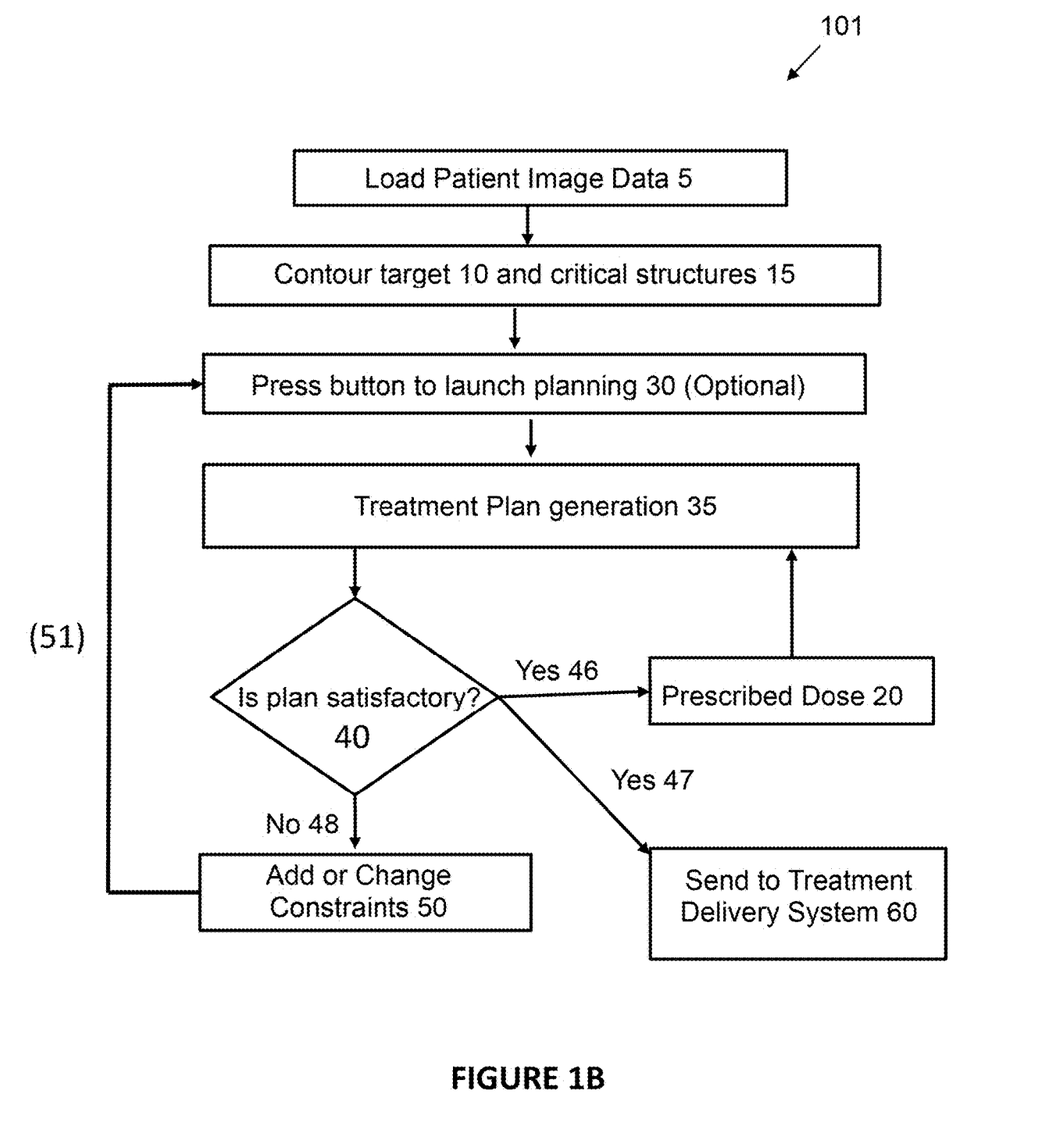
Figure 2:
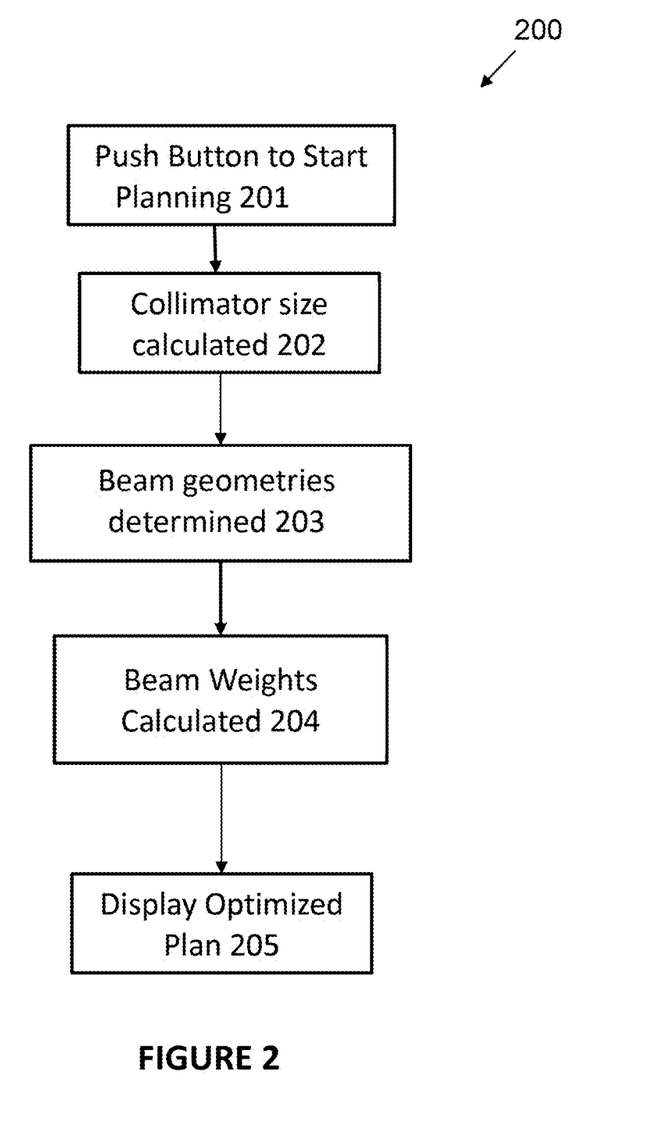
FIG. 2 illustrates basic steps in an exemplary treatment plan generation method, in accordance with some embodiments.

FIGS. 1A-1B depicts exemplary inverse planning processes that are accomplished by a series of steps. First, a user loads patient data into workstation (5). Next, the user contours to define the spatial extent of targets (10). The user can also contour to define the spatial extent of sensitive non-targets (15). It is appreciated that these contours can be performed by the user in a conventional manner, or assisted partly or entirely by the automated system. Next, the user defines the minimum dose to the target allowable (20). Then, as shown in FIG. 2, the system then performs target analysis and selects the ideal collimator (202). The system can also select additional collimators smaller than the ideal collimator. The isocenters are then identified (e.g., "Candidate Isocenters", "Potential Isocenters"). The system then determines the beam geometries 203 (e.g., trajectories), and the beam weights (45) are calculated. The system then displays the optimized plan to the user for confirmation or adjustment as desired.

Target analysis can be performed by examining a previously contoured target (segmented, for example into tumor and non-tumor regions) in an imported image series. In some embodiments, the dimensions of the target are approximated by an ellipsoid with the lengths of the three major axes identified. The ideal collimator is selected based on the target dimensions identified, for example, an ideal collimator can be approximately 0.75 mm*(length of the smallest major axis). The user can then select a smaller collimators (e.g., two or more smaller collimators that are immediately smaller than the ideal collimator), or larger collimators, or some combination thereof. So, for example, if the length of the smallest major axis is 22 mm, then 0.75*22=16.5 mm. The system will choose the nearest available collimator diameter as the "Ideal Collimator", in this example, potentially a 15 mm collimator. The user or the automated system can select other collimators as the candidates, for example, 10 mm and 7.5 mm collimators. Fractions or factors other than 0.75* may also be used, as can the middle/largest major axis (rather than the smallest) or some combination thereof. Optionally, the user can select collimator sizes manually as desired.

In one example, the candidate isocenters are identified, and the geometry of each beam is selected by the system. The candidate plan isocenters are placed randomly, thus in an approximately uniform distribution, on the target's boundary, or inside, or in some combination thereof. In order to achieve this, all of the points on the boundary (and/or the interior) can be digitized by choosing a resolution parameter (e.g., 0.5 mm). These points, separated by the resolution, can then be added into a comprehensive list of points and their coordinates. For each candidate isocenter to be placed, a point is selected in this list using a random number generator. For example, if there are 1000 points on the boundary of the target, and a number between 1 and 1000 is randomly generated, the first candidate isocenter is at this point. This point is then removed from the list, such that only 999 points remain on the list. A second random number is then generated, but this time between 1 and 999, thereby determining the placement of the second candidate isocenter at this point. That point is then removed from the list, leaving 998 points in the list. This iterative process is continued.

A number of variations of this process can be used. One variation on this process is to use the distance of a point from the boundary. For example, if the distance is zero, then it is exactly the boundary. If it is positive, say 1 mm, then the target can be reduced in size by 1 mm and use the boundary of the reduced target. If it is negative, say −1 mm, then the target can be enlarged by 1 mm. Another variation on this process is to change the resolution parameter. An algorithm that can automatically select the resolution parameter can be employed. Larger targets (e.g., >20 mm) can use larger resolution (e.g., 2 mm), while smaller targets (e.g., <5 mm) can use smaller resolution (e.g., 0.5 mm). Optionally, the user can also manually choose the resolution parameter.

Another variation on this process is changing the number of points removed from the list after placing an isocenter. An alternative way to accomplish this is to remove all the points in the list that fall within the collimator.

In another aspect, the weight of each beam contributing to the plan can be given its weight by the system. To achieve this, the target boundary is assigned the prescription dose of radiation (typically, by the user), and 0 radiation dose is assigned everywhere else (automatically unless elsewhere specified). In some embodiments, a linear programming technique can be used to quickly identify, for each beam, the monitor units (MUs), which are a measure of quantity of ionizer radiation. MUs per beam are a common form of expression of beam weight.

The process of beam weight determination is, an optimization problem in which the objective is to minimize a function while meeting the constraints, such as delivering a requisite dose to the target. A general optimization problem can be stated as follows:

Find x=(x1, x2, . . . xn)
To Minimize J(x)
With the following set of constraints $$C1(x)<=D1 \text{(can be>=as well)}$$

$$C2(x)<=D2$$

$$C3(x)<=D3$$

. . .

wherein xi is the dose in MU for each beam, Ci are the constraints and J(x) is the function being minimized, which can include $w_i$ (weights). By setting $w_i$ to 1, the total MUs delivered for the plan are minimized while meeting constraints including delivering prescription dose to the target.

In an exemplary case of inverse planning, x(1, 2, 3 . . . ) are the MUs per each beam, which the automated system computes. $J(x)=(w_1*x_1+w_2*x_2+ \ldots +w_n*xn)$. If $w_i$ is set to 1, then J(x) is the total dose delivered by the linear accelerator to the patient. In this case, the system seeks to minimize that total dose. Constraints (represented by C(1, 2, 3 . . . )) are used to designate that the dose needs to be greater than or equal to the designated prescription dose of ionizing radiation. Dose, in turn, is a function of MUs that must be delivered from the radiation source, and is represented by $x_1$, $x_2$, $x_3$, . . . . Constraints can be placed on the boundary of the target or critical structure, inside the target or critical structure, upon individual beams, or upon one or more manually designated points. When on the boundary, the constraint will be labelled C(x)>=Rx at the first point on the boundary. This can be repeated for every point on the boundary (e.g., at a given resolution). Each point on the boundary of the target can also specify a maximum dose. This constraint can be expressed as C(x)<=Rx at the same point. If both of the constraints above are used, then C(x)=Rx is requested at that point. When inside a critical structure, a constraint may also be expressed as C(x)<=D (the maximum dose allowed at that point)). For each beam, constraints can be placed to ensure that one or more beams do not dominate the plan, by specifying a designated maximum (e.g., each beam xi>=0, and xi<=MU max). Optionally, the user can also arbitrarily place manually selected points in the anatomy and specify a constraint (e.g., minimum or maximum) to increase or decrease the dose at that point.

In another aspect, to enhance the user experience, the system can determine any or all of these constraints automatically. For example, for targets, the system, by default, can automatically place constraints with minimum and maximum doses to be exactly equal to a nominal prescription dose (e.g., 1600 cGy) on the boundary and at one point in the center. In some embodiments, the system can place constraints based on a given distance (e.g., 5 mm) from the target. In the example herein, these constraints are specified as $C(x)<=0$. Specifying $C(x)$ as $<=0$ is a way of saying that the desired dose at that point is 0 dose, since the dose cannot be negative. For critical structures, the system can automatically place constraints with 0 dose as the maximum. For each beam, the system can choose the MU max (e.g., 200), which can also be user adjustable. As seen in the above automation example, the system selects 1600 and 0 for doses in the targets or critical structures, respectively, and nothing else. Therefore the target boundary is assigned to the prescription dose, and 0 dose is assigned everywhere else.

As a result of the advantages provided by embodiments of the invention, several notable benefits become tangible. Relative to forward planning, inverse planning, fewer number of beams are required, since each is optimized in its placement. As a result, processing times to deliver the solution are faster, typically 30% faster. Additionally, the role of the human expert is preserved in this system. By design, the system provides the flexibility to augment or replace with user-defined isocenter placement, beam placement and weight decisions. Constraints, including point constraints may be manually overridden and redefined as needed. This problem is exemplified as follows:

| Structure | | Dose | Priority |
|---|---|---|---|
| Target | >= | Rx min | P1 |
| Target | <= | Rx max | P2 |
| Critical 1 | <= | C1 | W1 |
| Critical 2 | <= | C2 | W2 |
| Critical 3 | <= | C3 | W3 |
| Critical 4 | <= | C4 | W4 |
| Critical 5 | <= | C5 | W5 |
| Critical 6 | <= | C6 | W6 |
| Critical 7 | <= | C7 | W7 |
| Critical 8 | <= | C8 | W8 |

In a conventional treatment planning system, before treatment planning, the clinician must input various treatment plan constraints, for example those noted above.

The above problem can be simplified, in accordance with the approach described herein so as to minimize the total dose to the patient with minimal interaction by the user in regard to setting values, etc., for example by a single interaction (e.g., selection of a treatment planning button) on the user interface. This simplified problem can be exemplified as follows:

| Structure | | Dose | Priority |
|---|---|---|---|
| Target | >= | Rx | Very High |
| Target | <= | Rx | High |
| Critical 1 | <= | 0 | Low |
| Critical 2 | <= | 0 | Low |
| Critical 3 | <= | 0 | Low |
| Critical 4 | <= | 0 | Low |
| Critical 5 | <= | 0 | Low |
| Critical 6 | <= | 0 | Low |
| Critical 7 | <= | 0 | Low |
| Critical 8 | <= | 0 | Low |

In some embodiments, Rx can be a nominal number automatically chosen by the system, since the user evaluation of the plan quality does not depend on this number, as the user only evaluates plan by looking at the isodose curves, DVHs, and various indices, which do not depend on the choice of this one number. By this approach, the treatment plan can be generated without the clinician entering any treatment plan constraints. Optionally, the system can allow the clinician to enter one or more constraints if desired, such that if a clinician prefers to use a more conventional treatment planning approach this is still an option. Accordingly, the system provides improved versatility allowing both treatment plan generation without any clinician input constraints, preferable for clinician's with limited experience, and treatment plan generation with one or more clinician input constrains, preferable for more experienced users.

Thus, the automated inverse planning system can automatically determine an optimal geometry (e.g., gantry position relative to patient, and hence beam trajectories), collimator size and beam weight (e.g., time spent on each beam and/or intensity of that beam). These aspects are optimized in accordance with any of the following aspects: (i) minimize the time required to deliver the treatment to the patient, (ii) maximize the quality of the plan as measured by certain parameters (e.g., conformality index, homogeneity index, gradient index), (iii) minimize the dose delivered to the whole patient, while delivering no less than the prescribed dose to the target), and (iv) ensure the tumor receives between a minimum and a maximum dose specified by the user, and (v) ensure critical structures must not get more dose than that specified.

In another aspect, prioritization of one or more the above aspects/requirements ensures that the system can always arrive at a treatment plan solution, since a rigid set of multiple requirements can often make a system that is unable to reach a solution. In some embodiments, in order to set these priorities, a constraint table based upon a general-purpose template can be implemented for each patient treatment case. Such a table requires at least a single number be provided in order to calculate a solution, namely the prescription dose to the target, such as a tumor. Typically, that dose number is provided by the user, although it is appreciated that the number can also be obtained from a table or a function based on information of the target tumor.

In some embodiments, the system can also obtain additional numbers/parameters, such as a maximum dose to critical structures, which can be pre-specified, obtained from look-up tables or functions or set by the user. Effectively all other parameters of the treatment plan, including but not limited to geometry, gantry position relative to patient, and hence beam trajectories, beam weights, can be calculated by the system. Optionally, one or more of these aspects can be adjusted or pre-selected by the user. Advantageously, the system allows a user to obtain an optimized treatment plan from the automated system upon obtaining the prescription dose by a single user interaction (e.g., select treatment planning button). Alternatively, the system can be designed so that treatment planning is fully automated and does not require any user interaction to initiate. In some embodiments, the system initiates treatment planning upon receiving or determining the target geometry, or upon the user updating the target geometry. In some embodiments, the system repeatedly perform treatment plan upon any adjustment or refinement of the target geometry by the user or the system.

Typically, the data sets depicting the external and internal anatomy of a patient (usually MRI, CT, or PET) are manually contoured or automatically segmented to spatially demarcate the radiation "target" (e.g., tumor) and optionally, any critical structures in which radiation exposure must be avoided or strictly limited can also be segmented within the image volume. Segmentation may occur via automated processes or a combination of image analysis techniques including thresholding, zero crossing, component labeling, boundary-based approaches including zero-crossings, run-length connectivity, dilation, erosion, hole filling, filtering, or matching with templates including flexible deformable models. Based upon the attributes of each of these structures, they will be categorized as to their identity (e.g., tumor, brainstem, trigeminal nerve root, optic nerve, optic chiasm, cochlea).

In another aspect, the system is configured to allow mixing and matching of automated processes with user-selected parameters. In some embodiments, the automated system is configured to identify the isocenter, and enable manual planning actions to be retained and incorporated into the constraints considered by the automated inverse planning process. Inverse planning process is continuously updated with the manually imposed designations and constraints. For example, the system may initially survey the spatial distribution of the target structure and critical structures. If the target is substantially spherical, an automated inverse-planning approach may be most efficient. If the target is irregular, such as a "dumbbell" shaped with much of the volume located far from the geometric center, applying a template-based planning approach may be most efficient.

Figure 3:
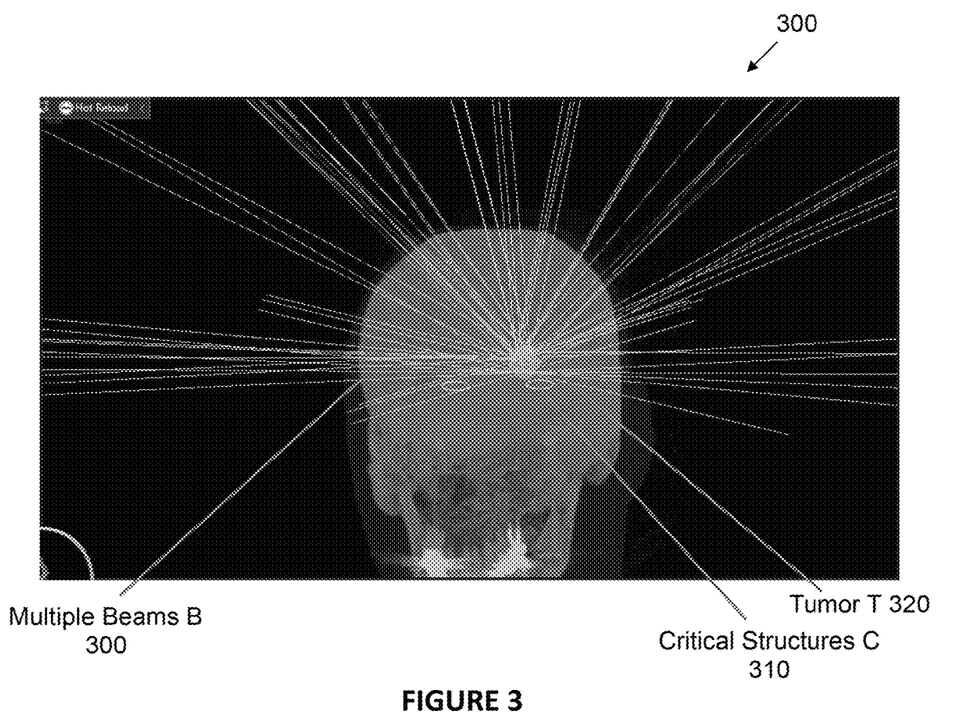
FIG. 3 illustrates an example user interface of the system, in accordance with some embodiments.

In some embodiments, an inverse planning process may generally proceed as follows. The system determines a plan so that an objective function J is minimized while meeting the constraints on doses in tumor(s) and other critical structures. Given a tumor region T and a critical region C, as shown in FIG. 3, the inverse planning problem is formulated as follows:

Find the plan X with beams that minimizes the objective function J(x) such that:

$DT(x) \leq D_{Tmax}$ for each pixel in Tumor $T$ $DT(x) \geq D_{Tmin}$ for each pixel in Tumor $T$ $Dc(x) \leq D_{Cmax}$ for each pixel in Critical Structure $C$ The objective function J itself can be defined in different ways depending on the planning system. The optimization variables X can also vary depending on the planning system. In some embodiments, the treatment planning system uses the objective function J as the total monitor units of all the beams. The selection of the linear objective function and the linear formulation of constraints enable optimization using linear programming.

In some embodiments, the inverse-planning process may be well suited for the user (e.g., physician or the physicist) to specify the doses required to kill a tumor and optionally the maximum doses allowed in the critical structures. An inverse planning process to specify the dose distributions based on the anatomy region may be referred to as region-based inverse planning. One of the assumptions of the region-based inverse planning is that the objective function is intelligently formulated such that the result of the optimization while meeting the user specified constraint criteria results in an overall optimal dose distribution. An optimal dose distribution, in the most ideal sense, is the uniform dose in the tumor equaling D, and 0 everywhere else. While this may not always be practical as an absolute requirement, the optimization strives to achieve this goal, the best it can, based on the objective function.

In another aspect, the system enables the user to control these characteristics. In some embodiments, the system allows the user to specify which beams (e.g., a first subset of the systems beams) should be selected using forward planning, and which beams (e.g., a second subset of system's beams) should be selected using inverse planning. Each beam in the first subset may be characterized by user-generated values representative of radiation emission point, target point, orientation, and radiation dose weight. Thus, each beam in the first subset is generated using forward planning. Each beam in the second subset may be generated using inverse planning. The radiation emission point, target point, orientation, and radiation dose weight for the beams in the second subset are generated by the system (e.g., treatment planning module) in such a way that at least a portion of a desired radiation dose distribution profile is achieved. For example, the user may produce a plan generated by a forward planning approach, by adjusting beam weights based on a selection of one or more beams. Alternatively, the user can produce a plan generated by the inverse planning approach, by using only beams selected based on one or more specific characteristics of the beams. Further alternatively, the user can use a partial set of beams generated using a forward planning approach, and the rest by one or more inverse planning approach.

In this manner, the treatment planning process is automated such that a single user interaction with the user interface of the system (e.g., a single mouse click or key stroke) can launch the process of treatment planning once the requisite information (e.g., treatment dose, target) has been input or obtained by the system and produce an optimized treatment plant suitable for therapy. Alternatively, the system can automatically launch treatment planning upon receiving the necessary information. This approach is simple, modern and elegant. However, because no single automated solution is best for every case, the system remains capable of generating treatment plans with additional user inputs to allow a more traditional, manual user-dependent mode.

FIGS. 1A-1B illustrates overviews of exemplary treatment planning methods, which can be performed by the automated system. As shown in FIG. 1A, method 100 first includes loading of patient image data 5. The system then obtains the contours 10 of the target and optionally the critical structures. The contours are determined from the image data and can be supplied to the system by the user, can be determined entirely by the system and confirmed by the user, or can be interactively determined by the user with the system. The prescribed dose 20 is then obtained by the system. The prescribed dose can be supplied by the user, or can be obtained from a lookup table or function and confirmed by the user. The user then performs a single interaction, such as pressing a button (physical or virtual) to launch treatment planning 30. In response to the single interaction, the system automatically generates the treatment plan 35 (see also FIG. 2). This single interaction step is optional, since in some embodiments, treatment planning may be launched automatically. Once the treatment plan is generated, it is determined whether the plan is satisfactory. If the plan is confirmed by the user to be satisfactory, then the treatment plan is sent to the treatment delivery system 70 for subsequent delivery to the patient. If it is determined by the user that the plan is not satisfactory, the user can add or change constraints 50, which can include constraining or adjusting one or more parameters, which are then fed back 51 into the automated plan generation to produce another treatment plan. This process is repeated as needed until a satisfactory plan is generated as confirmed by the user. FIG. 1B illustrates another example method 101 similar to that in FIG. 1A, except including some aspects of iterative forward planning in regard to obtaining the prescribed dose 20 upon confirming a satisfactory plan 46, which is then fed back into plan generation. If the user considers the plan is not satisfactory 48a, the user can add or change constraints 50 which are fed back 51 into the plan generation of an updated treatment plan, until the user confirms the plan is satisfactory 47, after which the plan is sent to the treatment delivery system 60.

FIG. 2 depicts an exemplary method 200 of automatically generating a treatment plan in accordance with embodiments of the invention. In plan generation method 200, after a single user interaction (e.g., clicking a button to start planning 201), the automated system determines collimator size 202, determines beam geometries 203, determines beam weights 204, and then displays the optimized treatment plan 205 to the user. This single interaction step is optional, since in some embodiments, treatment planning may be launched automatically. If the user determines the plan is satisfactory, the plan is sent to the treatment delivery system. If the user determines the plan is not satisfactory, the user can add or change constraints in regard one or more parameters and/or in regard to prioritization or weighting of parameters constraints. The plan generation process can then be repeated in response to the user again initiating treatment planning until the user determines the treatment plan is satisfactory. Alternatively, this process can be automatically repeated upon any adjustment or update to the target geometry.

FIG. 3 depicts an exemplary treatment plan 300 in accordance with some embodiments. The treatment plan includes collimator sizes, beam weights, and the associated trajectories of multiple beams 300 to achieve the prescribed treatment dose of radiation to the target tumor 320 while minimizing radiation exposure to select critical structures (e.g., optic nerves).

Figure 4:
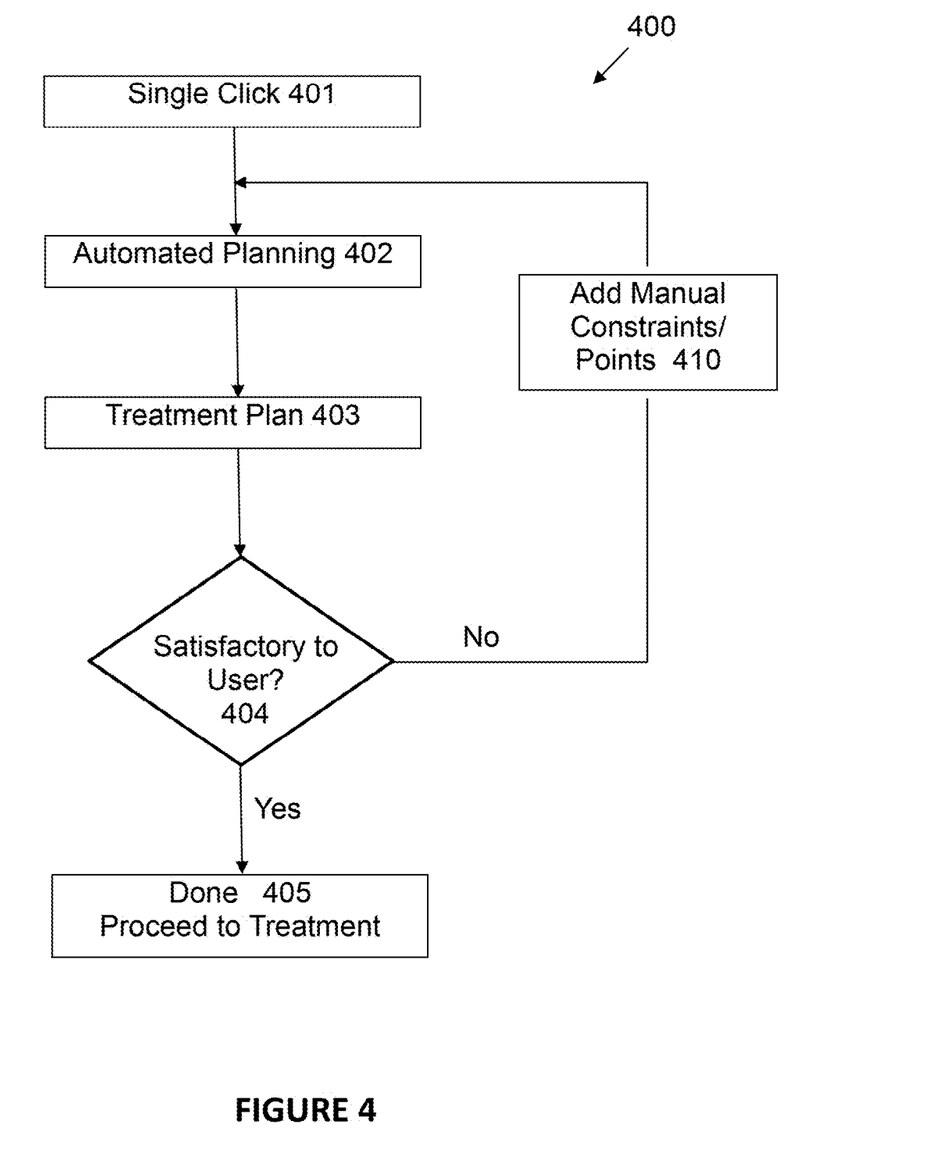
FIG. 4 illustrates a workflow of a treatment planning method, in accordance with some embodiments.

FIG. 4 depicts a workflow diagram 400 of treatment planning in accordance with some embodiments. The workflow includes a single click or actuation 401 on a user interface of the system by the user, which initiates an automated planning procedure 401 to generate a treatment plan 403, which is performed in a single iteration of the automated planning process. The treatment plan 403 is then presented to the user for review and a decision input 404. If the treatment plan is not satisfactory, then the user is provided the option to produce another treatment plan, for example, by adding manual constraints 410 to the plan, which are then fed back into the automated planning 402 procedure, which in another iteration, produces an updated treatment plan according to the added constraints. The constraints can include one or more parameters, as described herein (e.g., collimator sizes, beam weights, beam number, beam trajectories, beam intensities, points, etc.). Once the treatment plan is satisfactory, the user confirms and the planning is complete 405 and the plan is then utilized in treatment delivery.

Figure 5:
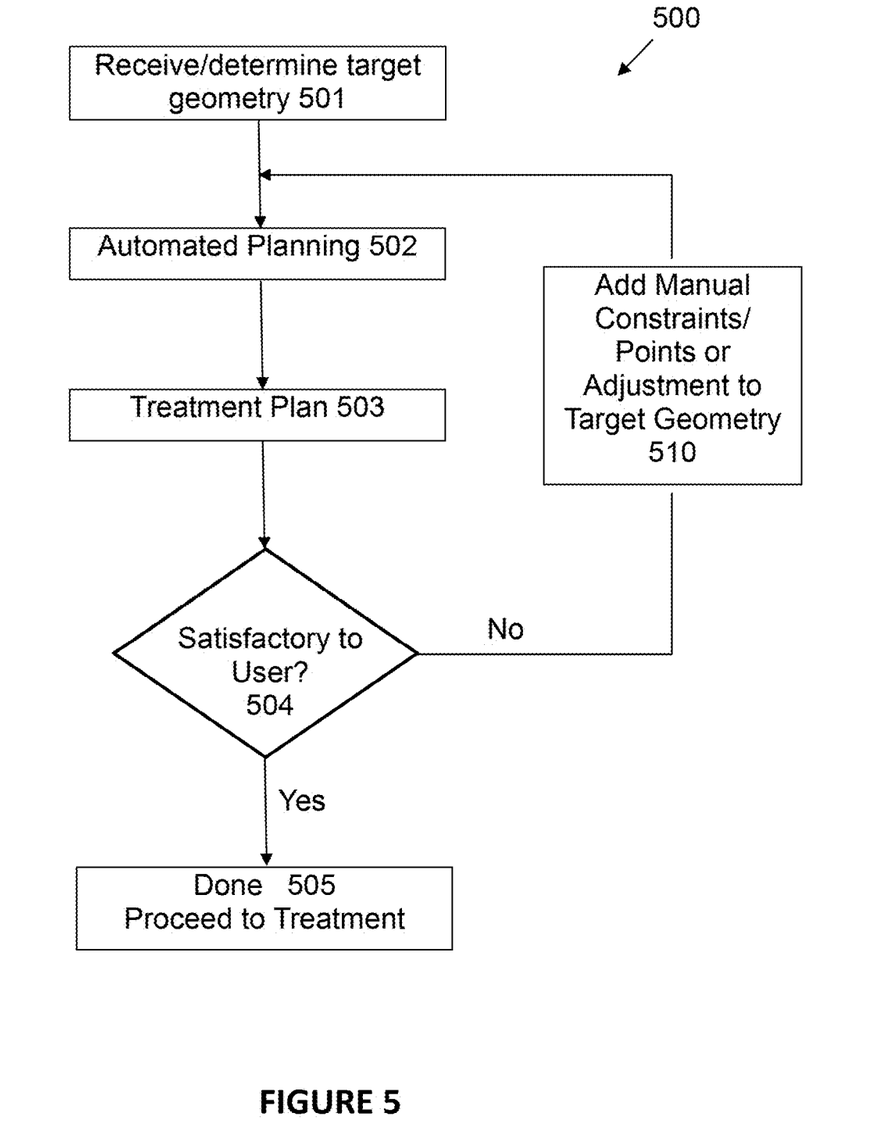
FIG. 5 illustrates a workflow of a treatment planning method, in accordance with some embodiments.

FIG. 5 depicts a workflow diagram 500 of treatment planning in accordance with some embodiments. The workflow includes receiving or determining a target geometry 501 by the system or input by the user, which initiates an automated planning procedure 501 to generate a treatment plan 503, which can be performed in a single iteration of the automated planning process. The treatment plan 503 is then presented to the user for review and a decision input 504. If the treatment plan is not satisfactory, then the user is provided the option to produce another treatment plan, for example, by adding manual constraints to the plan or by updating or refining the target geometry 510, which are then fed back into the automated planning 502 procedure, and in another iteration, produces an updated treatment plan according to the added or updated constraints. The constraints can include one or more parameters, as described herein (e.g., collimator sizes, beam weights, beam number, beam trajectories, beam intensities, points, etc.). Once the treatment plan is satisfactory, the user confirms and the planning is complete 505 and the plan is then utilized in treatment delivery.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art. Any references cited herein are incorporated by reference in their entirety for all purposes.

What is claimed is:

1. A method for generating a treatment plan for a radiation treatment delivery planning system, the method comprising:
   receiving or obtaining, with the system, a set of patient imaging information regarding a patient;
   receiving or determining a target geometry of a target based on the set of patient imaging information; and
   upon initiation of treatment planning, automatically generating, utilizing programmable instructions recorded on a memory of or accessed by the system, a treatment plan based on the set of patient imaging information and the target geometry based on the set of patient imaging information without requiring any user input treatment plan parameters or constraints,
   wherein upon the initiation of treatment planning without any prior user input of treatment plan parameters or constraints, the system automatically generates the treatment plan utilizing inverse planning; and
   wherein upon initiation of treatment planning after user input of one or more treatment plan parameters or constraints, the system automatically generates the treatment plan utilizing, at least in part, forward planning based on the one or more treatment plan parameters or constraints previously input;
   whereby the system accommodates differing approaches of treatment planning according to a clinician's preference.

2. The method of claim 1, wherein the treatment plan is generated in response to the system receiving or determining the target geometry.

3. The method of claim 2, wherein automatically generating the treatment plan comprises determining optimal beam geometries, beam size, beam weight.

4. The method of claim 1, wherein the treatment plan is generated in response to receiving one or more user interactions via a user interface of the system.

5. The method of claim 4, wherein the one or more user interactions of the user interface comprises a single user interaction to initiate treatment planning.

6. The method of claim 5, wherein the single user interaction to initiate treatment planning comprises a single click of a button or virtual button on a graphical user interface display.

7. The method of claim 4, wherein the one or more user interactions comprises a single user interaction to initiate treatment planning and one or more additional user interactions to select or adjust one or more parameters of treatment planning.

8. The method of claim 7, wherein the one or more parameters of treatment planning include any of: beam geometries, beam size, beam weight, or any combination thereof.

9. The method of claim 1, wherein the treatment plan is further based on a treatment dose input by the user.

10. The method of claim 1, wherein the treatment plan is determined without a particular treatment dose and scaled to achieve a desired treatment dose.

11. The method of claim 1, wherein the one or more treatment plan parameters or constraints pertain to any of: beam number, beam directions, beam size, beam weights, and beam intensities.

12. The method of claim 1, wherein automatically generating the treatment plan is performed in a single iteration or automated process.

13. The method of claim 12, wherein the single iteration or automated process does not require further user input beyond an initial user interaction initiating treatment plan generation.

14. The method of claim 1, wherein receiving or obtaining the set of patient imaging information comprises loading a patient medical image of a patient record system.

15. The method of claim 1, wherein receiving or obtaining the target geometry comprises receiving contours of the target geometry derived from the set of patient imaging information.

16. The method of claim 1, wherein receiving or obtaining the target geometry comprises assisting a user in determining contours of the target geometry from the set of patient imaging information.

17. The method of claim 1, wherein automatically generating the treatment plan comprises determining optimal beam geometries, beam size, beam weight to determine an optimal treatment plan.

18. The method of claim 17, further comprising:
storing the optimal treatment plan in a record in the system.

19. The method of claim 1, further comprising:
continuously updating the treatment plan upon receiving or determining updated target geometry or upon receiving any additional user input of one or more treatment plan parameters or constraints.

20. The method of claim 1, wherein the treatment plan is generated for an image-guided radiation treatment system utilizing an X-ray LINAC as a radiation source.

21. The method of claim 20, wherein the X-ray LINAC is mounted on a gantry and rotatable around the patient such that the LINAC delivers multiple treatment beams to the target from many angles around a treatment sphere.

22. The method of claim 1, further comprising:
displaying on a graphical user interface display the generated treatment plan including a graphical depiction of the target and a plurality of beam trajectories to the target.

23. The method of claim 1, whereby the system accommodates differing approaches of treatment planning according to a clinician's preference without requiring the user switch between differing implementations.

24. A system for generating a treatment planning for therapeutic radiation delivery, the system comprising:
a component that receives a set of patient imaging information regarding a target;
a user interface configured to receive one or more user interactions; and
a treatment planning component that, utilizing programmable instructions recorded on a memory of or accessed by the system, automatically generates a treatment plan based on the patient imaging information without requiring any user input treatment plan constraints, wherein the treatment planning component is configured to generate the treatment plan by inverse planning when no treatment plan constraints are input, and configured to generate the treatment plan utilizing forward planning and/or a combination of inverse and forward planning based on any treatment plan constraints input prior to initiating treatment planning.

25. A method for generating a medical treatment plan with an automated planning generation system, the method comprising:
receiving patient information regarding a patient with the system, the patient information including a patient identifier;
persistently storing the patient identifier in the system in which the treatment plan is created;
displaying information identifying the patient and/or treatment and displaying an indication of a single action that is to be performed by the user by a user to generate the treatment plan;
in response to the single action being performed, sending to the system a request to initiate treatment planning generation based on the patient information and a target geometry without requiring user input treatment plan constraints; and
displaying the generated treatment plan to the user for confirmation by the user.

26. The method of claim 25, further comprising:
upon receiving confirmation of the plan, sending the treatment plan to a treatment delivery system.

27. The method of claim 25, further comprising:
upon receiving input to adjust constraints or parameters by the user, repeating treatment plan generation and displaying an updated treatment plan for confirmation to the user.

28. The method of claim 25, wherein the single action to initiate treatment planning comprises a single click of a button or virtual button on a graphical user interface display.

* * * * *